(12) United States Patent
Gehlsen et al.

(10) Patent No.: US 6,498,181 B1
(45) Date of Patent: Dec. 24, 2002

(54) SYNERGISTIC TUMORCIDAL RESPONSE INDUCED BY HISTAMINE

(75) Inventors: Kurt R. Gehlsen, Encinitas, CA (US); Kristoffer Hellstrand, Göteborg (SE); Svante Hermodsson, Mölndal (SE)

(73) Assignee: Maxim Pharmaceuticals, San Diego, CA (US)

( * ) Notice: Subject to any disclaimer, the term of this patent is extended or adjusted under 35 U.S.C. 154(b) by 0 days.

(21) Appl. No.: 09/226,226

(22) Filed: Jan. 6, 1999

(51) Int. Cl.[7] .................... A61K 31/415; A61K 39/395; A61K 39/40; A61K 39/42
(52) U.S. Cl. .................................. 514/396; 424/142.1
(58) Field of Search ........................ 514/396; 424/142.1

(56) References Cited

U.S. PATENT DOCUMENTS

| | | |
|---|---|---|
| 5,432,168 A | 7/1995 | Brandes ........................ 514/90 |
| 5,618,846 A | 4/1997 | Brandes ........................ 514/641 |
| 5,728,378 A | 3/1998 | Hellstrand et al. .......... 424/85.7 |
| 5,747,543 A | 5/1998 | Brandes ........................ 514/651 |

FOREIGN PATENT DOCUMENTS

| | | |
|---|---|---|
| EP | 0 282 002 A2 | 9/1988 |
| WO | WO 91 04037 A | 4/1991 |
| WO | WO 93/14754 | 8/1993 |
| WO | WO 93/24144 | 12/1993 |
| WO | WO 96/05231 | 2/1996 |
| WO | WO 96/05289 | 2/1996 |
| WO | WO 97/22357 | 6/1997 |
| WO | WO 97 22357 A | 6/1997 |
| WO | WO 97 42968 A | 11/1997 |

OTHER PUBLICATIONS

Dröge, W. et al., "Histamine Augments Interleukin–2 Production and the Activation of Cytotoxic T Lymphocytes," *Immunopharmacology*, Elsevier Science Publishers, 11 (1986) pp. 1–6.

Abbas, et al., eds., Cellular and Molecular Immunology, W.B. Saunders Co., Philadelphia, pp. 349–350, 1991.

Ashley, et al., *Journal of Neuro–Oncology*, 35:259–273, 1997, "Monoclonal antibodies to growth factors and growth factor receptors: their diagnostic and therapeutic potential in brain tumors."

Burtin, et al., *Cancer Letters*, 12:195–201, 1981, "The Influence of Intraperitoneal Injections of Histamine on Tumor Growth in Fibrosarcoma–Bearing Mice."

Dverak, et al., *Cancer Cells*, 3(3):77–85, Mar. 1991, "Structure of Solid Tumors and Their Vasculature: Implications for Therapy with Monoclonal Antibodies."

Eary, J.F. and O.W. Press, *Recent Results in Cancer Research*, 141:177–182, 1996, "High Dose Radioimmunotherapy in Malignant Lymphoma."

Frankel, et al., *Cancer Biology*, 6:307–317, 1995, "Clinical Trials of Targeted Toxins."

Hacker, N.F. and M.E.L. van der Burg, *Annals of Oncology*, 4(supp 4):S17–S22, 1993, "Debulking and Intervention Surgery."

Hellstrand, et al., *Scand J Clin Lab Invest*, 57:193–202, 1997, "Histamine in Cancer Immunotherapy."

Larson, et al., *ACTA Oncologica*, 32(7/8):709–715, 1993, "Recent Achievements in the Development of Radiolabeled Monoclonal Antibodies for Diagnosis, Therapy and Biologic Characterization of Human Tumors."

Mach, et al., *Current Opinion in Immunology*, 3:685–693, 1991, "Imaging and Therapy with Monoclonal Antibodies in Non–Hematopoietic Tumors."

Majno, et al., *Journal of Cell Biology*, 42:647–672, 1969, "Endothelial Contraction Induced by Histamine–Type Mediators."

Matzku, S., *Recent Results in Cancer Research*, 141:1–8, 1996, "Monoclonal Antibodies in Tumor Therapy."

Mayhan, William G., *Am. J. Physiol.*, 266(Heart Circ. Physiol. 35): H2369–H2373, 1994, "Nitric Oxide Accounts for Histamine–Induced Increases in Macromolecular Extravasation."

Norton, Jeffrey A., *Digestion*, 55(suppl 3):98–103, 1994, "Surgical Management of Carcinoid Tumors: Role of Debulking and Surgery for Patients with Advanced Disease."

O'Donoghue, J.A., *Recent Results in Cancer Research*, 141:77–99, 1996, "Optimal Therapeutic Strategies for Radioimmunotherapy."

Osband, et al., *The Lancet*, pp. 636–638, Mar. 21, 1981, "Successful Tumor Immunolotherapy with Cimetidine in Mice."

Quak, J. and G. van Dongen, *Eur Arch Otorhinolaryngol*, 251:1–5, 1994, "Current Perspectives in the Use of Monoclonal Antibodies for Detection and Treatment of Head and Neck Tumors."

Reynolds, et al., *European Journal of Surgical Oncology*, 23:224–227, 1997, "Histamine Content in Colorectal Cancer. Are There Sufficient Levels of Histamine to Affect Lymphocyte Function?".

Reynolds, et al., *British Journal of Surgery*, 85:538–541, 1998, "Histamine in Human Breast Cancer."

(List continued on next page.)

Primary Examiner—Jerome D. Goldberg
(74) Attorney, Agent, or Firm—Knobbe, Martens, Olson & Bear, LLP

(57) ABSTRACT

The present invention relates to methods of treating cancer in which histamine is administered in conjunction with other cancer therapies. The cancer therapy includes surgery, radiation, immunotherapy, the administration of an agent which enhances the humoral immune response of the patient or any combination thereof.

1 Claim, No Drawings

OTHER PUBLICATIONS

Sautter–Bihl, M.D. and H. Bihl, *Recent Results in Cancer Research*, 141:123–135, 1996, "Can Preirradiation Enhance Tumor Uptake of Radiolabeled Pharmaceuticals? Experimental Data in a Mouse Neuroblastoma Xenograft System."

Sedelacek, H.H., *Critical Reviews in Oncogenesis*, 5(6):555–587, 1994, "Vaccination for Treatment of Tumors: A Critical Comment."

Slingluff, Craig L. Jr and Hilliard F. Seigler, *Annals of Plastic Surgery*, 28(1):104–107, 1992, "Immunotherapy for Malignant Melanoma with a Tumor Cell Vaccine."

Steel, Gordon G., Basic Clinical Radiobiology 2nd Edition, pp. 1–7, Copyright 1997, "Introduction: The Significance of Radiobiology for Radiotherapy."

Steel, Gordon G., Basic Clinical Radiobiology 2nd Edition, pp. 8–13, Copyright 1997, "The Growth Rate of Tumors."

Tüting, et al., *J Mol Med*, 75:478–491, 1997, "Gene–Based Strategies for the Immunotherapy of Cancer."

Wong, John F., *Circle*, No. 38, Jul. 1998, "Therapeutic Applications Grow in Promise and Number."

Hansson, Brune, et al., "NK cell–mediated killing of AML blasts: role of histamine, monocytes and reactive oxygen metabolites," European Journal of Haematology, vol. 57, pp. 312–319, 1996.

Dröge, et al., "Histamine Augments Interleukin–2 Production and the Activation of Cytotoxic T Lymphocytes," *Immunopharmacology*, 11:1–6, 1986.

Huhnt, W., et al., "Growth, microvessel density and tumor cell Invasion of human colon adenocarcinoma under repeated treatment with hyperthermia and serotonin," *J. Cancer Res. Clin. Oncol.* 121:423–428, 1995.

Janevik–Ivanovska, E., et al., "Bivalent Hapten–Bearing Peptides Designed for Iodine–131 Pretargeted Radioimmunotherapy," *Bioconjugate Chem.*, 8:526–533, 1997.

Johansson, S., et al., "The response of Dunning R3327 prostatic adenocarcinoma IL–2, histamine and radiation," *Br. J. Cancer*, 77(8):1213–1219 (1998).

De Santes et al., Cancer Res. (1992), 52(7), 1916–23 Abstract Only.*

* cited by examiner

SYNERGISTIC TUMORCIDAL RESPONSE INDUCED BY HISTAMINE

FIELD OF THE INVENTION

The present invention relates to methods of treating cancer in which histamine is administered in conjunction with other cancer therapies. The cancer therapy includes surgery, radiation, immunotherapy, the administration of an agent which enhances the humoral immune response of the patient or any combination thereof.

BACKGROUND OF THE INVENTION

Despite tremendous advances over the past several years, current cancer therapies fail to cure many forms of cancer. The problems faced by investigators and clinicians are numerous. Some tumors are not resectable or do not respond to radiation or chemotherapy or combinations of these procedures. Furthermore, the severe morbidity often associated with these treatments has led many to look for entirely new approaches to tumor therapy that are more specifically lethal for cancer cells and less toxic for normal cells. Attempts to promote an immune response to the tumor by immunizing the cancer patient with killed cancer cells or antigens specific for cancer cells have been largely unsuccessful and the use of monoclonal antibodies (mAbs) as the "magic bullet" to specifically destroy cancer cells without harming normal cells remains clinically limited. Methods that enhance the effectivity of known cancer therapies are desperately needed.

Surgery is touted by many to be the only potentially curative therapy for patients suffering from stomach, pancreatic, carcinoid and ovarian tumors. (Norton, *Digestion* 55(suppl 3):98–103 (1994)). Although surgery is often the indicated treatment for malignant disease, this form of cancer therapy has two major shortcomings. First, many tumors are not resectable because they are located in or have spread into vital structures. (Dvorak et al., *Cancer Cells* 3: 77–85 (1991)). While debulking of tumors in vital areas has been presented as an alternative, such procedures are felt by many to inadequately treat the disease and only improve the quality of life of the patient. (Norton, *Digestion* 55(suppl 3):98–103 (1994)). Second, by the time of diagnosis and removal of the primary tumor, many tumors have already metastasized. (Dvorak et al., *Cancer Cells* 3: 77–85 (1991)) and (Norton, *Digestion* 55(suppl 3):98–103 (1994)). Metastases, which tend to be multiple and wide spread, do not easily lend themselves to surgical excision and, consequently, many patients undergo major surgical procedures only to have rapid disease progression found soon after surgery. (Dvorak et al., *Cancer Cells* 3: 77–85 (1991)). While surgery remains a good first line of defense against cancer, oncologists are now also combining other treatment methods including radiation, chemotherapy and immunotherapy to obtain better patient survival. (Hacker and van der Burg, *Annals of Oncology* 4 (suppl. 4): S17–S22 (1993)).

External beam radiation has replaced surgery for the long-term control of many tumors of the head and neck, cervix, bladder, prostate and skin, in which it often achieves a reasonable probability of tumor control with good cosmetic result. (*Basic Clinical Radiobiology* 2nd edition. Steel ed., Arnold Publishers, pp. 1–13 (1997)). External beam radiation is generally helpful for the treatment of localized tumors but this approach is also problematic because it causes considerable damage to surrounding cells and compromises the patient's immune system. The use of radioactive "seed implants" has provided more focus on tumor cells and less damage to surrounding tissue but a more specific means to deliver radiation to the tumor is needed. While radiation therapy is a good alternative to surgery, it is unable to treat a large percentage of cancers that are radiation-insensitive and, because of the high morbidity associated with high doses of external beam radiation, the use of radiation to treat metastastic disease is not desirable. (Dvorak et al., *Cancer Cells* 3: 77–85 (1991)).

Many forms of antibody therapy to treat cancer have also been reported. Early antibody therapy treatments relied almost entirely on complement fixation to kill tumor cells. (*Cellular and Molecular Immunology*. Eds. Abul K Abbas, Andrew H. Lichtman, and Jordan S. Pober, W. B. Saunders Co., Philadelphia (1991)). Recently, greater success has been achieved using antibodies which block cancer cell growth factor receptors. (Wong, *Genetic Engineering News* pp.23 and 49 (July 1998) and Ashley et al., *J of Neuro-Oncology* 35:259–273 (1997)). The use of antibody conjugates which bind tumor cells with cytotoxic substances such as toxic molecules or radioisotopes has also seen promising results. (Larson et al., *ACTA Oncologica* 32:709–715 (1993); Quack and van Dongen, *Eur Arch Otorhinolaryngol* 251:1–5 (1994); Frankel et al., *Cancer Biology* 6:307–317 (1995); Mach et al., *Curr Op in Immunol* 3:685–693 (1191) and *Recent Results in Cancer Research vol 141:Systemic Radiotherapy with Monoclonal Antibodies*. edited by M. L. Sautter-Bihl and M Wannenmacher, Springer-Verlag publishers, (1996)). Another innovative antibody treatment for cancer uses antibody heteroconjugates—dual purpose antibodies which direct bound cancer cells to phagocytic cells of the immune system. (Wong, *Genetic Engineering News* pp.23 and 49 (July 1998)). Preliminary clinical trials with mAb heteroconjugates have shown promise in the treatment of renal and prostate cancer. (Id.).

Although a variety of tumor cells can be lysed in vitro by antibody-dependent mechanisms such as complement activation or antibody-dependent cell-mediated cytotoxicity, few therapies based on enhancing the humoral response of a subject have been clinically successful. (Sedlacek, *Critical Reviews in Oncogenesis* 5(6):555–587 (1994)). In one study, patients suffering from melanoma were administered a vaccine containing a mixture of three allogenic melanoma cell lines and showed a 71% 10-year actuarial survival as opposed to the 40% 10-year actuarial survival demonstrated by melanomic patients who received a single cell line vaccine. (Slingluff and Seigler, *Ann Plast Surg* 28:104–107 (1992)). In another study, however, leukemic patients immunized with killed leukemia cells failed to demonstrate any significant improvement. (*Cellular and Molecular Immunology*. Eds. Abul K Abbas, Andrew H. Lichtman, and Jordan S. Pober, W. B. Saunders Co., Philadelphia (1191)).

In an attempt to improve cancer vaccines, researchers have tried numerous strategies to make the cancer cell vaccines more antigenic. (Sedlacek, *Critical Reviews in Oncogenesis* 5(6):555–587 (1994)). Studies on immunization with plasmid DNA encoding defined tumor antigens or with a complex comprising hydrophobized polysaccharides attached to an oncogenic receptor protein, for example, may show greater clinical success. (Tuting et al., *J Mol Med* 75:478–491 (1997) and Gu et al. *Cancer Research* 58:3385–3390 (1998)). At present investigators have had limited success with treating cancer by administering agents which enhance the humoral response of the patient and approaches to improve the effectivity of this form of treatment are needed.

Despite recent progress in cancer therapy, many problems persist. Tumors often metastasize, grow in sensitive areas and are not treatable by surgery or radiation. (Dvorak et al., *Cancer Cells* 3: 77–85 (1191)). Tumor cells also generally avoid immunosurveillance in the cancer patient and most current vaccines poorly trigger a cancer patient's immune system to overcome this immunotolerant state. (Sedlacek; *Critical Reviews in Oncogenesis* 5(6):555–587 (1994)). Further, the use of antibody therapies such as immunotoxins, immunoradionuclides, immunoheteroconjugates, and receptor specific antibodies has been limited by low-level expression of the targeted tumor associated antigen, low-affinity mAbs, inefficient radionuclides, non-specific toxicity of the antibody conjugate and poor tumor uptake of the therapeutic agent. (Ashley et al., *J of Neuro-Oncology* 35:259–273 (1997); Frankel et al., *Cancer Biology* 6:307–317 (1995); Mach et al., *Curr Op in Immunol.* 3:685–693 (1191) and Sedlacek, *Critical Reviews in Oncogenesis* 5(6):555–587 (1994)). The need for an agent that enhances current methods of cancer therapy has long been manifest.

SUMMARY OF THE INVENTION

The present invention provides novel methods of treating cancer in which histamine is administered in conjunction with conventional cancer therapies such as surgery, radiation, immunotherapy, and agents which enhance the humoral immune response of the patient. In one embodiment, a method of augmenting a cancer therapy encompasses administering to a subject a pharmaceutically acceptable form of histamine over a period of time such that a blood histamine concentration sufficient to augment the cancer therapy is achieved and administering to the subject a cancer therapy such as surgery, radiation, immunotherapy and an agent which enhances the humoral response of the subject.

Preferably, a pharmaceutically acceptable form of histamine is used such as histamine, histamine dihydrochloride, histamine phosphate, histamine salts, esters, congeners, prodrugs, histamine receptor agonists and diphenyleneiodonium. The types of radiation therapy which can be used include external beam radiation, radionuclides, radioactive implants, radioactive antibodies, radioactive lipids, radioactive proteins, radioactive glycolipids and radioactive glycoproteins. The types of immunotherapy which can be used include the administration of a monoclonal antibody, a humanized monoclonal antibody, an Fab, an (Fab')$_2$, an Fv, an antibody conjugate, an Fab conjugate, an (Fab')$_2$ conjugate, an Fv conjugate and an antibody heteroconjugate. Several types of agents which enhance the humoral response of the subject can be used including viral antigens, cancer cell antigens, inactivated cancer cells, vaccines, and vitamers.

Histamine is administered in such a manner that a stable blood histamine concentration is maintained during the administration of the cancer therapy to the subject. Histamine can be administered to the subject indirectly by administering a substance which induces the release of endogenous histamine such as retinoic acid, a retinoid, IL-3 or an ingestible allergen. Histamine can be administered prior to administering the cancer therapy, after administering the cancer therapy, or during administration of the cancer therapy. Furthermore, histamine is administered in a dose from 0.1 to 10.0 milligrams per day.

In another embodiment, the invention provides a method of screening cancer treatments in which a non-human mammal, having been grafted with human tumor cells, is administered histamine and a cancer therapy, such as a radioactive substance, an antibody, an agent that enhances the humoral immune response of the non-human mammal, radiation, or surgery. After administering the cancer therapy, the tumorcidal response of the non-human mammal is then determined at various time points. According to this method, monoclonal antibodies, monoclonal antibodies conjugated to a compounds such as a toxin, a radioactive substance, a radionuclide, an antibody fragment or a second antibody, a vaccine (including killed cancer cells), a radioactive seed implant or external beam radiation can be used.

DETAILED DESCRIPTION OF THE PREFERRED EMBODIMENT

Histamine is a biogenic amine, i.e., an amino acid that possesses biological activity mediated by pharmacological receptors after decarboxylation. The role of histamine in immediate-type hypersensitivity is well-established. (Plaut, M. and Lichtenstein, L. M, 1982, Histamine and Immune Responses in *Pharmacology of Histamine Receptors*. Ganellin, C. R. and M. E. Parsons, eds. John Wright & Sons, Bristol, pp. 392–435). Histamine also mediates arteriole dilation which causes a rise in capillary and venule pressure. (Majno et al., *J Cell Bio* 42:647–672 (1969)). Furthermore, histamine induces contraction of endothelial cells resulting in the formation of intercellular gaps and extravasation of blood vessels. (Id.).

The present invention is based on the unexpected discovery that histamine produces a synergistic tumorcidal response when it is administered in conjunction with surgery, radiation, antibody therapy or agents which enhance the humoral response of a cancer patient.

By "histamine" is meant histamine, its dihydrochloride salt (histamine dihydrocholride), histamine phosphate, other histamine salts, esters, or prodrugs, and histamine receptor ($H_1$, $H_2$, $H_3$) agonists. Seratonin, bradykinin, diphenyleneiodonium and 5HT agonists are also contemplated. Other analogs of histamine or histamine receptor agonists that are suitable for use in the present invention are disclosed in U.S. Pat No. 5,728,378 and are known to those of skill in the art. The administration of compounds which induce the release of endogenous histamine from the patient's own tissues are also included within the scope of the present invention; thus, the term "histamine" as used herein incorporates these compounds as well.

By "cancer therapy" is meant surgery, radiation, chemotherapy, antibody therapy and agents which enhance the humoral immune response of a patient suffering from cancer. "Cancer therapy" may also include combinations of the treatments mentioned above. It will be appreciated by those skilled in the art that several combinations of the above cancer therapy methods produce synergistic effects on malignancies. Optimization of such combination treatment protocols in conjunction with histamine treatment, as detailed below, would be routine.

By "surgery" is meant surgical procedures to remove cancer cells from a patient including but not limited to tumor resection and/or debulking of a tumor. Established methods of surgical oncology vary according to the type of tumor and the patient's particular situation. Examples of surgical techniques are found in *Surgical Oncolog* edited by Raphael E. Pollock; Kluwer Academic Publishers, 1997.

By "radiation therapy" is meant the application of external beam radiation or the administration of radioactive substances to a cancer patient including but not limited to radionuclides, radioactive implants, radioactive antibodies or radioactive proteins. Many approaches to radiation therapy are known in the art and examples can be found in

*Basic Clinical Radiobiology* (*second edition*), edited by G. Gordon Steel, Arnold publishers, 1997.

By "antibody therapy" is meant the administration of an antibody, an antibody conjugate or an antibody heteroconjugate to a cancer patient for the purpose of treating or preventing cancer. Many forms of antibody therapy are known in the art including, but not limited to, the administration of monoclonal or humanized monoclonal antibodies, the administration of toxin or radionuclide conjugated antibodies and the administration of monoclonal antibody heteroconjugates having one domain that binds to a cancer antigen and another domain that binds to the Fc region of IgG. Further, the term antibody therapy is meant to include the administration of (Fab')$_2$ or Fab fragments with or without conjugated toxins or radionuclides. Several examples of antibody therapy are found in *Recent Results in Cancer Research vol* 141:*Systemic Radiotherapy with Monoclonal Antibodies*, edited by M. L. Sautter-Bihl and M. Wannenmacher, Springer-Verlag publishers, 1996.

By "agents which enhance the humoral immune response" is meant substances which are administered to a cancer patient for the purpose of enhancing their humoral immune response. Many methods of enhancing the humoral immune response of a patient suffering with cancer are known, including but not limited to, the administration of viral antigens, cancer cell antigens, inactivated cancer cells, vaccines and vitamers including ascorbic acid, tocopherol and betacarotene.

The administration of histamine can follow several treatment regimens and the following protocols are meant to exemplify some of the ways to use the present invention but they are not intended to limit the scope of the present discovery. The present invention includes the delivery of a beneficial amount of histamine to the cancer patient before, during or after the administration of an established form of cancer therapy such as surgery, radiation, antibody therapy or an agent which enhances the humoral immune response of the patient.

Beneficial levels of circulating blood histamine are obtained by administering histamine at a dosage of around 0.1 to 10.0 mg/day, preferably around 0.5 to 8.0 mg/day and more preferably around 1.0 to 5.0 mg/day. In a further embodiment, the histamine is administered over a period of 1–4 weeks. In a highly preferred embodiment, the histamine is administered for a period of 1–2 weeks. In one embodiment of the invention, a beneficial stable level of circulating blood histamine concentration (i.e a stable level of circulating blood histamine concentration of at least about 0.2 $\mu$M) is maintained.

It will be appreciated by those of skill in the art that the patient's circulating blood histamine level can also be monitored during the course of treatment and boosted whenever the level drops below the beneficial level or approaches the lower limits of the beneficial level. For example, in this embodiment, histamine can be administered whenever the subject's histamine levels drop below 0.2 $\mu$M. Alternatively, it will be appreciated that histamine can be administered at periodic intervals at dosages sufficient to establish and maintain beneficial levels.

Routes and carrier compositions for administering histamine have been disclosed in U.S. Pat, Nos. 5,348,739 and 5,728,378, which are incorporated herein by reference. Controlled release vehicles are also well-known to those of skill in the pharmaceutical sciences. The technology and products in this art are variably referred to as controlled release, sustained release, prolonged action, depro, repository, delayed action, retarded release and time release; the words "controlled release" as used herein is intended to incorporate each of the foregoing technologies. U.S. patent application Ser. No. 08/767,338 also discloses numerous controlled release vehicles as well as infusion devices for use in the administration of histamine.

Preferably, the histamine is injected, infused or released into the patient at a rate of from about 0.5 to 0.2 mg per minute. A rate of about 0.1 mg per minute is preferred. The histamine is preferably administered over a period of time ranging from about 1, 3 or 5 minutes to about 30 minutes, with an upper limit of about 20 minutes being preferred, such that the total daily adult dose of histamine ranges from between about 0.1 to about 10.0 mg, with about 1.0 to about 5.0 mg being preferred. Histamine administered over longer periods of time (i.e., longer than about 30 minutes) has been found to result in a decrease or lack of efficacy, while rapid administration over less than 1 to 3 minutes can cause more pronounced and serious sides effects, which include anaphalaxis, heart failure, broncospasm, pronounced flushing, discomfort, increased heart rate and respiratory rate, hypertension, and severe headache.

Administration of each dose of histamine can occur from once a day to up to about four times a day, with twice a day being preferred. Administration can be subcutaneous, intravenous, intramuscular, intraoccular, oral, transmucosal, or transdermal, and can utilize direct hypodermic or other injection or infusion means, or can be mediated by a controlled release mechanism of the type disclosed above. Any controlled release vehicle or infusion device capable of administering a therapeutically effective amount of histamine over a period of time ranging from about 1 to about 30 minutes can be used.

In addition to histamine, histamine dihydrochloride, histamine phosphate, or other histamine salts, esters, congeners, prodrugs and histamine receptor agonists, the use of seratonin, 5HT agonists, and compounds which induce the release of histamine from the patient's own tissues is also included within the scope of the present invention. Retinoic acid, other retinoids such as 9-cis-retinoic acid and all-trans-retinoic acid, IL-3 and ingestable allergens are compounds which are known to induce the release of endogenous histamine. These compounds can be administered to the patient by oral, intravenous, intramuscular, subcutaneous or other approved routes. However, the administration of the compound which induces the release of histamine from the patient's own tissue should result in a release of endogenous histamine in the range of from about 0.1 to 10.0 mg/day , preferably around 0.5 to 8.0 mg/day and more preferably around 1.0 to 5.0 mg/day.

Administration of each dose of a compound which induces histamine release can occur from once per day to up to about 4 times per day, with twice per day being preferred. Administration can be subcutaneous, intravenous, intramuscular, intraoccular, oral, transmucosal, or transdermal, and can incorporate a controlled released mechanism of the type disclosed above. Any controlled release vehicle capable of administering a therapeutically effective amount of a compound which induces histamine release over a period of time ranging from about 1 to about 30 minutes can be used.

Malignancies against which the treatment may be directed include, but are not limited to, primary and metastic malignant solid tumor disease, and hematological malignancies such as acute and chronic myelogenous leukemia, acute and chronic lymphatic leukemia, multiple myeloma, Waldenstrom's macroglobulinemia, hairy cell leukemia, myelodysplastic syndrome, polycytaemia vera, and essential thrombocytosis.

The present invention can be better understood by way of the following examples which are representative of the preferred embodiments but which are not to be construed as limiting the scope of the invention.

Blood Histamine Levels Can Be Raised and Maintained at a Beneficial Level Following Histamine Administration To practice the present invention, beneficial levels of histamine must be raised in a subject suffering from a malignant disease. The following example provides one approach to establish stable beneficial levels of circulating blood histamine in a cancer patient.

EXAMPLE 1

Five patients suffering from acute myleogenous leukemia (AML) in remission received treatment with histamine dihydrochloride diluted in sterile sodium chloride. Histamine was administered morning and night at separate subcutaneous injection sites over a period of 21 consecutive days. The histamine was given as subcutaneous injections using 1 ml syringes containing 0.1 mg of histamine per ml. The histamine treatment was given twice daily (morning and night) at a dosage of 0.4 to 0.7 mg histamine per injection (i.e., a daily total dose of histamine of 0.8 to 1.4 mg per day).

Peripheral blood venous samples were drawn in 10 ml heparinized test tubes before the onset of treatment and weekly thereafter. The samples were drawn at least 8 hours after the last injections of histamine. The concentration of histamine in the whole blood samples was analyzed by the use of a double antibody radioimmunoassay kit obtained from Bionerica, Inc., Newport Beach, Calif. 92663 (catalog number 1051). The manufacturer's instructions provided with the kit, dated June, 1989, were followed. Blood histamine levels were measured at the indicated times.

The patients exhibited blood histamine levels of less than 0.2 $\mu$M at the start of the experiment. Following histamine administration, circulating blood histamine levels rose to beneficial levels (i.e a stable level of circulating blood histamine concentration of at least about 0.2 $\mu$M). Surprisingly, the circulating blood histamine levels remained elevated for sustained periods of time, even after histamine administration was discontinued. The results of this experiment demonstrated that blood histamine levels can be raised and maintained at a beneficial level following histamine administration.

This ability to raise circulating blood histamine levels in a patient suffering from a malignancy disease, and maintaine the histamine concentration at a beneficial level, can be combined with methods of cancer therapy as detailed in EXAMPLES 2, 3, 4, and 5 below.

Cancer Therapy Employing a Combination of Histamine and Surgery

As contemplated by the present inventors, histamine is administered in conjunction with surgical resection of the tumor so as to achieve a synergistic tumorcidal response in the patient. By one approach, histamine is administered before surgery for a sufficent time to raise the stable concentration of histamine in the patient's blood to at least about 0.2 $\mu$M. Surgical removal of the tumor is then performed according to standard techniques. (See for example, *Surgical Oncolog*, edited by Raphael E. Pollock, Kluwer Academic Publishers, 1997). After the tumor burden has been removed, histamine therapy is continued for a time sufficient to conclude that a complete response to the tumor has been achieved. Depending on the type of malignancy, several methods of determining the persistance of cancer cells are available including the detection of shed cancer cell-specific antigens by ELISA or in situ detection of cancer cells using radiolabeled antibodies and imaging techniques. (Quak and van Dongen, *Eur. Arch. Otorhinolaryngol* 251:1–5(1994)).

EXAMPLE 2

A synergistic tumorcidal response is obtained by administering histamine before, during and after surgical removal of a prostate tumor. Accordingly, a pharmaceutically acceptable form of histamine in a sterile carrier solution is injected subcutaneously into a patient suffering from prostate cancer for one week (0.5–2.0 mg per day) prior to surgery. After this period of treatment and when circulating blood histamine levels have increased to at least 0.2 $\mu$M, surgical resection of the tumor burden is performed.

Once the tumor is removed, circulating levels of blood histamine are maintained at at least about 0.2 $\mu$M until a complete response is observed. The tumorcidal response is evaluated by determining the level of PSA antigen in the patient over time according to conventional methods. By employing the method disclosed in this example, a synergistic tumorcidal response is observed and prostate cancer is effectively treated.

Cancer Therapy Employing a Combination of Histamine and Radiation Treatment

In another embodiment, histamine is administered in conjunction with radiation therapy so as to achieve a synergistic tumorcidal response in the patient. By one approach, histamine is administered before radiation therapy for a sufficent time to raise the stable concentration of histamine in the patient's blood to at least about 0.2 $\mu$M. The tumor is then subjected to external beam radiation according to standard techniques. (Seefor example, *Basic Clinical Radiobiologu (second edition)*, edited by G. Gordon Steel, Arnold publishers, 1997). Histamine therapy is continued until a complete response is observed, as determined above. Further treatment of radiation can also be administered in conjunction with histamine therapy if tumor regression is not readily apparent.

EXAMPLE 3

A synergistic tumorcidal response is obtained by administering histamine before, during and after radiation treatment of a prostate tumor. Accordingly, a pharmaceutically acceptable form of histamine in a sterile carrier solution is injected subcutaneously into a patient suffering from prostate cancer for one week (0.5–2.0 mg per day) prior to radiation therapy. After this period of treatment and when circulating blood histamine levels have increased to at least 0.2 $\mu$M, the tumor burden is subjected to external beam radiation (60–70 Gy).

Once the tumor has been irradiated, circulating levels of blood histamine are maintained at least 0.2 $\mu$M until a complete response is observed. The tumorcidal response is evaluated by determining the level of PSA antigen in the patient over time according to conventional methods. By employing the method disclosed in this example, a synergistic tumorcidal response is observed and prostate cancer is effectively treated.

Cancer Therapy Employing a Combination of
Histamine and Antibody Therapy

In another embodiment of the present invention, histamine is administered in conjunction with an antibody therapy. According to one aspect of this embodiment, a radioactive monoclonal antibody is administered in conjunction with histamine. Preferably, histamine is administered for 1–2 weeks before the antibody therapy to raise the stable concentration of histamine in the patient's blood to at least about 0.2 $\mu$M. After a stable level of blood histamine of at least bout 0.2 $\mu$M has been achieved, a radiolabeled mAb directed to a cancer cell antigen is administered in conjunction with histamine treatment to the patient. (See for example, *Recent Results in Cancer Research vol 141:Systemic Radiotherapy with Monoclonal Antibodies*, edited by M. L. Sautter-Bihl and M Wannenmacher, Springer-Verlag publishers, 1996). Histamine treatment may be continued until a complete response is observed, as determined above.

Radiolabelled mAbs specific for a tumor antigen are prepared by labeling the antibody with an isotope or combinations of isotopes, such as $^{131}$I, $^{90}$Y, $^{67}$Cu, $^{186}$Re, $^{188}$Re, $^{212}$Bi or $^{211}$At. Preferable radiolabeled mAbs are able to deliver more than 6000 rads to the tumor and have sufficient affinity so that the patient's bone marrow is not exposed to more than 300 rads. $^{131}$I labeled anti-B1 (Bexxar) mAb, raised to the CD-20 antigens that are expressed on the surface of mature B-cells, is one example of a radiolabeled mAb that has seen successful in treating follicular non-Hodgkins lymphoma in recent clinical trials. (Wong, *Genetic Engineering News* pp.23 and 49 (July 1998)). Use of $^{131}$I labeled anti-B1 (Bexxar) mAb, as well as other radiolabeled mAbs, in conjunction with histamine treatment is within the scope of this embodiment.

In another aspect, heteroconjugate mAbs which direct the bound cancer cell to the phagocytic cells of the immune system are used in conjunction with the histamine treatment protocol detailed above. For example, the mAb MDX-210 (Medarex) which comprises one domain that binds the proto-oncogene HER-2/neu (C-erbB2), the cell-surface growth factor p185$^{HER-2}$ receptor with partial homology to the epidermal growth factor (EGF) receptor, and a second domain which recognizes the Fc receptor for high affinity IgG that activates and guides natural killer cells (NK) of the immune system to the disease site has been shown to be an effective treatment for renal and prostate cancer. (Wong, *Genetic Engineering News* pp.23 and 49 (July 1998)). The present inventors contemplate the use of this and similarly designed heteroconjugate antibodies in conjunction with the administration of histamine to obtain a synergistic tumorcidal response.

Another use included in this embodiment of the present invention involves the administration of humanized mAbs raised against cancer cell-specific receptors. The p185$^{HER-2}$ receptor (Genetech), for instance, has been shown to block binding of epidermal growth factor to the receptor and, thus, shut-off the subsequent transducing signal for cell proliferation. (Wong, *Genetic Engineering News* pp.23 and 49 (July 1998)). In clinical trials with the p185$^{HER-2}$ antibody, breast cancer patients have exhibited significant improvement in overall tumor response. The use of humanized mAbs raised against the p185$^{HER-2}$ receptor (Genetech) and other mAbs directed to cancer cell-specific receptors in conjunction with histamine treatment are also contemplated by the present inventors.

EXAMPLE 4

A synergistic tumorcidal response is obtained by administering histamine before, during and after antibody treatment of a patient suffering with breast cancer. Accordingly, a pharmaceutically acceptable form of histamine in a sterile carrier solution is injected subcutaneously into the patient for one week (0.5–1.0 mg per injection 1–2 times per day) prior to antibody therapy. After this period of histamine treatment, the patient is administered humanized $^{131}$I labeled p185$^{HER-2}$ antibody (Genetech) and histamine therapy is continued.

Once the tumor has been treated with the antibody, circulating levels of blood histamine are maintained at least 0.2 $\mu$M until a complete response is observed. The tumorcidal response is evaluated by determining the level of p185$^{HER-2}$ receptor in the patient over time according to conventional methods. (Quak and van Dongen, *Eur. Arch. Otorhinolaryngol* 251:1–5(1994)). By employing the method disclosed in this example, a synergistic tumorcidal response is observed and breast cancer is effectively treated.

Cancer Therapy Employing a Combination of
Histamine and Approaches to Enhance a Humoral
Immune Response in a Cancer Patient A further embodiment of the present invention involves the administration of an agent which enhances the humoral immune response of a patient in conjunction with histamine therapy. By one approach, histamine is administered before the agent is provided to the patient so that a stable concentration of at least about 0.2 $\mu$M histamine in the patient's blood is initially established. An humoral immune response enhancing agent such as a viral antigen, a cancer cell antigen, an inactivated cancer cell, a vaccine or a vitamer is then administered to the patient. Histamine therapy is continued until a complete response is observed, as determined above. Further, the present inventors contemplate treatments with the agent which enhances the humoral immune response of the patient in conjunction with histamine therapy and the administration of cytokines known to enhance the cellular immune response.

EXAMPLE 5

A synergistic tumorcidal response is obtained by administering histamine before, during and after treatment of a patient suffering from melanoma with an agent that enhances the immune response. Accordingly, a pharmaceutically acceptable form of histamine in a sterile carrier solution is injected subcutaneously into the patient for one week (0.5–1.0 mg per injection 1–2 times per day) prior to administration of the agent that enhances the humoral immune response. After this period of histamine treatment and when circulating blood histamine levels have increased to at least 0.2 $\mu$M, the patient is administered a vaccine comprising a killed mixture of three melanomic cell lines according to standard techniques. (Slingluff et al., *Ann. Plast. Surg* 28:104–107 (1992)).

Once the tumor has been treated with the vaccine, circulating levels of blood histamine are maintained at least 0.2 $\mu$M until a complete response is observed. The tumorcidal response is evaluated by determining the presence of melanoma in the patient over time according to conventional methods. (Quak and van Dongen, Eur. *Arch. Otorhinolaryngol* 251:1–5(1994)). By employing the method disclosed in this example, a synergistic tumorcidal response is observed and the melanoma is effectively treated.

While the methods of EXAMPLES 2–5 detail several protocols which would produce a synergistic tumorcidal response by virtue of the administration of histamine in conjunction with established cancer treatments, many more cancer therapy protocols which take advantage of histamine induced synergism can be developed by using the screening method, or variation thereof, described in EXAMPLE 6.

Screening of Therapeutics for a Synergistic Tumorcidal Response when the Agent is Administered in Conjunction with Histamine Methods to screen therapeutics for their ability to produce a synergistic tumorcidal response when they are administered with histamine is another embodiment of the present invention. Generally, a model system for the cancer is first established, then histamine and the therapeutic agent are administered to the subject and the tumorcidal response is determined.

EXAMPLE 6

Preparation of a model system and a radiolabelled mAb is as follows. By example, human neuroblastoma xenografts are established by subcutaneous injection of about $10^6$ tumor cells of the human SK-N-SH neuroblastoma cell line (purchased from the American Type Culture Collection, Rockville Md.) into the right flank of nude mice. The cancer is allowed to proliferate until the tumor measures approximately 1 cm in diameter. The mAb BW575/9 (Behringwerke, Marburg, Germany) is a murine IgG1 isotype directed against the neural cell adhesion molecule (NCAM) and expressed by neurobalstomas, melanomas and other cancers. (Bosslet et al. European Pat. Pub. No. EP 0443 599 A2). BW575/9 has been reported to bind specifically to the neuroblastoma cell line SK-N-SH. (*Recent Results in Cancer Research vol* 141:Systemic Radiotherapy with Monoclonal Antibodies. edited by Sautter-Bihl and Wannenmacher, Springer-Verlag publishers, Bihl and Bihl, *Experimental Data in a Mouse Neuroblastoma Xenograft System* pp. 124–135 (1996)). As a control, the anti-idiotypic mAb B40 (purchased from the German Cancer Research Center, Heidelberg, Germany) is used. The mAbs are labeled with $^{131}$I by the Iodogen method to a specific activity of 1 $\mu$Ci/$\mu$g according to esatblished methods. (Id.).

To assess the synergistic tumoricidal response obtained by histamine therapy administered in conjunction with radioimmunotherapy, an experiment is conducted. A pharmaceutically acceptable form of histamine in a sterile carrier solution is injected into the tail vein of nude mice having a malignancy for one week (0.5 mg per day) prior to antibody treatment. One control group is not administered histamine so that the synergistic tumorcidal response of histamine therapy can be determined. After this period of histamine treatment and when circulating blood histamine levels have increased to at least 0.2 $\mu$M, the mice are administered 10 $\mu$Ci of $^{131}$I labeled mAbs by injection into the tail vein, according to standard techniques.

Mice are killed by cervical dislocation on 1, 4, 12, 24, 36 and 48 days after administration of the antibody therapy and the tumor, spleen, kidney, liver, muscle and bone are harvested, measured and analyzed in a multichannel gamma counter for $^{311}$I. Daily histamine treatment, as above, is continued during the course of the experiment and a second administration of the antibody is provided on day 24. The results of this experiment show that a greater tumorcidal response is obtained when the BW575/9 mAb is administered in conjunction with histamine than when the BW575/9 is administered by itself.

Using variations of the model system presented above, newly developed therapeutic agents and treatment protocols can be rapidly screened for their ability to produce synergistic tumorcidal response when they are administered or performed in conjunction with histamine treatment. Indeed, the appraoch used in EXAMPLE 6 can be used or readily adapted to screen other antibodies, antibody conjugates, antibody heteroconjugates, agents which enhance the humoral immune response of the subject, radiation therapies and surgical techniques.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. A method of therapy for a cancer sensitive to treatment with the combination of histamine and a cancer therapy is a subject comprising:

administering to said subject an amount of said cancer therapy sufficient to synergistically inhibit said cancer when combined with said pharmaceutically acceptable form of histamine, wherein the cancer therapy comprises $I^{131}$ labeled $_p$185 HER-2 antibody.

* * * * *

UNITED STATES PATENT AND TRADEMARK OFFICE
CERTIFICATE OF CORRECTION

PATENT NO.    : 6,498,181 B1
DATED         : December 24, 2002
INVENTOR(S)   : Gehlsen et al.

It is certified that error appears in the above-identified patent and that said Letters Patent is hereby corrected as shown below:

<u>Column 12,</u>
Line 38, cancel "is" and replace it with -- in --.

Signed and Sealed this

Fourth Day of March, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,498,181 B1
DATED : December 24, 2002
INVENTOR(S) : Gehlsen et al.

It is certified that error appears in the above-identified patent and that said Letters Patent is hereby corrected as shown below:

Column 1,
Line 4, please insert the following:

-- RELATED APPLICATIONS

The present application is related to and claims the benefit of U.S. Application Serial No. 08/767,338, filed on December 16, 1996, now U.S. Patent No. 6,221,893, which is a continuation-in-part of application No. 08/649,121, filed on May 14, 1996, now U.S. Patent No. 5,961,969. --

Signed and Sealed this

Twenty-eighth Day of September, 2004

JON W. DUDAS
*Director of the United States Patent and Trademark Office*